United States Patent [19]

Glover

[11] Patent Number: 4,557,928

[45] Date of Patent: Dec. 10, 1985

[54] ANTI-DANDRUFF CREAM RINSE CONDITIONER

[75] Inventor: David A. Glover, Carrollton, Tex.

[73] Assignee: Amway Corporation, Ada, Mich.

[21] Appl. No.: 547,927

[22] Filed: Nov. 2, 1983

Related U.S. Application Data

[63] Continuation-in-part of Ser. No. 395,502, Jul. 6, 1982, abandoned, which is a continuation-in-part of Ser. No. 302,100, Sep. 14, 1981, abandoned.

[51] Int. Cl.$^4$ ................................................. A61K 7/08
[52] U.S. Cl. ................................ 424/70; 424/DIG. 4; 514/166
[58] Field of Search ........................... 424/70, DIG. 4; 514/166

[56] References Cited

U.S. PATENT DOCUMENTS

| | | | |
|---|---|---|---|
| 1,860,320 | 5/1932 | Nordlander | 424/70 |
| 2,149,249 | 2/1939 | Nitsche | 252/6 |
| 3,236,733 | 2/1966 | Karsten et al. | 424/245 |
| 3,489,686 | 1/1970 | Parran, Jr. | 252/106 |
| 3,555,006 | 1/1971 | Storfer | 536/114 |
| 3,576,760 | 4/1971 | Gould et al. | 252/403 |
| 3,580,853 | 5/1971 | Parran, Jr. | 252/152 |
| 3,761,417 | 9/1973 | Parran, Jr. | 252/106 |
| 3,876,760 | 4/1975 | Nersesian et al. | 424/70 |
| 3,966,902 | 6/1976 | Chromecek | 424/59 |
| 4,027,008 | 5/1977 | Sokol | 424/62 |
| 4,061,602 | 12/1977 | Oberstar et al. | 424/70 |
| 4,150,115 | 4/1979 | Jacquet et al. | 424/70 |
| 4,185,106 | 1/1980 | Dittmar et al. | 424/263 |
| 4,210,161 | 7/1980 | Wagman | 424/70 |
| 4,224,339 | 9/1980 | Van Scott et al. | 424/289 |
| 4,379,753 | 4/1983 | Bolich, Jr. | 252/106 |

FOREIGN PATENT DOCUMENTS

| | | | |
|---|---|---|---|
| 0007704 | 2/1980 | European Pat. Off. | 424/70 |
| 0018717 | 11/1980 | European Pat. Off. | 424/70 |
| 0034385 | 8/1981 | European Pat. Off. | 424/70 |
| 2262375 | 6/1974 | Fed. Rep. of Germany. | |
| 1114110 | 12/1955 | France | 424/329 |
| 54-98343 | 8/1979 | Japan | 424/245 |
| 1385318 | 6/1974 | United Kingdom | 424/70 |
| 1196570 | 2/1975 | United Kingdom | 424/70 |

OTHER PUBLICATIONS

Cosmetics & Toiletries, 4/1979, pp. 61 to 69, vol. 94.
Hyde et al., Cosmetics & Toiletries, 4/1979, vol. 94, pp. 57 to 59.
Publication D&CI/Feb. 1980 "The Use of Merquat Polymers".
Meer Corporation & the Stein-Hall Publication entitled "What is Jaguar?".
Jetco Chemicals, Inc. Technical Data Bulletin No. 77-11.
"Evaluation of Efficacy of Antidandruff Agents," Journal Of The Society Of Cosmetic Chemists, vol. 32, No. 6, 1981.
Hercules Incorporated Publication, ©1974, "NATROSOL Hydroxyethyl Cellulose".

*Primary Examiner*—Dale R. Ore
*Attorney, Agent, or Firm*—Price, Heneveld, Huizenga & Cooper

[57] ABSTRACT

The specification discloses an anti-dandruff cream rinse conditioner based on zinc pyrithione, a cationic polymer, a suspension system consisting of (1) one of glucan gum, guar gum or mixtures thereof, and (2) hydroxyethylcellulose, as well as other optional conditioning agents and ingredients.

27 Claims, No Drawings

ANTI-DANDRUFF CREAM RINSE CONDITIONER

BACKGROUND OF THE INVENTION

This application is a continuation-in-part of application Ser. No. 395,502, filed July 6, 1982, which was a continuation-in-part of application Ser. No. 302,100, filed Sept. 14, 1981, both now abandoned.

The present invention relates to anti-dandruff compositions. Anti-dandruff shampoos have been sold in a variety of different formulations for a number of years. Many different types of anti-dandruff agents are employed. Insoluble particulate zinc pyrithione (or zinc pyridinethione) [zinc bis(2-pyridylthio)-n-oxide] has perhaps the most widely acknowledged efficacy as an anti-dandruff agent.

It has been suggested that cationic polymers can increase the efficacy of zinc pyrithione in anti-dandruff shampoos by enhancing the deposition and retention of the water insoluble zinc pyrithione particles on the hair and scalp. U.S. Pat. No. 3,489,686 suggests that polyethylenimine or the reaction product of polyethylenimine and ethylene oxide or propylene oxide performs such a function. U.S. Pat. No. 3,580,853 teaches that a cationic homopolymer comprising a particular cellulose derivative achieves this objective. U.S. Pat. No. 3,761,417 suggests a piperidinum chloride for this purpose.

It has also been suggested in the literature that an acrylamide copolymer of dimethyldiallyl ammonium chloride of a molecular weight of around 500,000, known by the trade name MERQUAT 550 and available from Merck & Co., Inc., might be useful in shampoos because it is said to contribute to detangling and improve wet and dry compatability without a greasy feeling. This acrylamide copolymer is said to impart richness and lubricity to the shampoo foam. This chemical is known in the art as Quaternium 41, per the C.T.F.A. Cosmetic Ingredient Dictionary, Second Edition.

Since this particular polymer is also cationic in nature, we thought to take advantage of both its shampoo improving qualities and its cationic properties, even though it is different from the cationic polymers cited in the patents above, to create a more desirable, and more efficacious zinc pyrithione anti-dandruff shampoo. Unfortunately, this combination was unsuccessful. We were unable to produce a commercially acceptable shampoo based on this acrylamide copolymer and zinc pyrithione.

The resulting shampoos were unstable and/or tended to be slimy. Indeed, we know of no commercial anti-dandruff shampoo based on this acrylamide copolymer, even though such use has been suggested. A cellulose thickener sold as Avicel GLG11, Quaternium 41 and zinc pyrithione were stable initially in a shampoo, but were granular, thick and not stable over a long period of time. Hydroxypropylmethylcellulose thickener (Methocel), Quaternium 41 and zinc pyrithione were initially stable, but not over long periods of time, unless excessive amounts of Methocel were used. Increasing Methocel amounts increases sliminess.

In addition to a large number of anti-dandruff shampoos, at least one anti-dandruff rinse has been marketed commercially. It did not utilize zinc pyrithione as its active anti-dandruff ingredient. Nor did it incorporate any conditioners of the type typically employed in cream rinse conditioners. We are unaware of any anti-dandruff rinse conditioners currently on the market.

Part of the problem in creating an anti-dandruff rinse conditioner is that some conditioners are cationic polymers, which seem to be incompatible with zinc pyrithione, particularly suspensions thereof. Beecham Group Ltd. claims in European Patent Publication No. 7704 that this can be overcome in a rinse conditioner by suspending the zinc pyrithione in a cationic polymer such as polymer JR, which is Quaternium 19 in the C.T.F.A. Cosmetic Ingredient Dictionary. We were unable to verify the results claimed by this patent publication, at least in any commercially acceptable embodiment.

Indeed from the paucity of anti-dandruff rinses and the total absence of anti-dandruff cream rinse conditioners available on the market, it appears that attempts to create anti-dandruff rinses and especially anti-dandruff rinses conditioners have generally been frustrated. Based upon our own work, we believe that attempts to create anti-dandruff rinses based on zinc pyrithione, which rinses also employ cationic conditioning polymers, have been frustrated due to the incompatibility of the cationic polymeric materials with zinc pyrithione and/or suspending agents used to keep the water insoluble zinc pyrithione in suspension.

SUMMARY OF THE INVENTION

Surprisingly, we have found that an anti-dandruff cream rinse conditioner can be made using hydroxyethylcellulose and either glucan gum or guar gum (or mixtures thereof) as the suspending ingredients, combined with zinc pyrithione and a cationic polymer. Yet, this combination was not effective in a shampoo formulation.

Indeed to our surprise, we discovered that even though the cationic acrylamide copolymer discussed above (Quaternium 41) did not work to commercial satisfaction in a zinc pyrithione shampoo, the aforesaid cationic acrylamide copolymer and zinc pyrithione do work exceptionally compatibly as an effective anti-dandruff conditioner rinse combination in the presence of glucan gum, guar gum or mixtures thereof and hydroxyethylcellulose. Indeed, the resulting anti-dandruff conditioner rinse shows surprisingly exceptional efficacy as an anti-dandruff composition. While anti-dandruff shampoos seem to require 2% active zinc pyrithione, the anti-dandruff cream rinse conditioner of the present invention was shown to be equally efficacious with only 1% acive zinc pyrithione, though obviously the amounts may vary.

These and other objects, advantages and features of the composition of the present invention will be more fully understood and appreciated by reference to the detailed specification and the appended claims.

DESCRIPTION OF THE PREFERRED EMBODIMENT

In the anti-dandruff cream rinse conditioner of the preferred embodiment, zinc pyrithione in an amount sufficient to act as an effective anti-dandruff agent is mixed with from about 0.25 to about 5.0% cationic polymer, as supplied by the manufacturer, in sufficient (1) glucan gum, guar gum or both and (2) hydroxyethylcellulose to keep these active ingredients in a smooth, consistent suspension. Up to as much as 18% in other conditioning agents are also most preferably used to give the product conventional cream rinse properties.

Miscellaneous additives may also be used such as jojoba oil, perfume and the like. All percentages herein are by weight unless otherwise indicated.

As used above and as used throughout this entire disclosure and claims, the percent by weight of cationic polymer is the percent by weight of that cationic polymer as it is supplied by the manufacturer. For example, Quaternium 41, the preferred cationic polymer, is supplied by Merck & Co., under the mark MERQUAT 550, as an 8% aqueous solution. Quaternium 40, a substitute for Quaternium 41, is supplied by Merck & Co. under the mark MERQUAT 100, as a 40% aqueous solution. Quaternium 23, another substitue, is supplied by GAF, under the mark GAFQUAT 734, as a 50% alcohol solution. Quaternium 19, still another substitute, is supplied by Union Carbide, under the mark POLYMER JR, as a dry powder. And finally, Polyquaternium 3, another substitute, is supplied by the Richardson Co., under the mark CATAMER Q, as a 30% aqueous solution.

The most preferred cationic polymer is identified in the C.T.F.A. Cosmetic Dictionary as Quaternium 41. It is an acrylamide copolymer of dimethyldiallyl ammonium chloride and has a molecular weight of approximately 500,000. It gives the most markedly preferred commercial product. This is particularly surprising in that we were unable to formulate this cationic polymer into an anti-dandruff shampoo formulation using zinc pyrithione. Shampoo formulations based on this cationic polymer were granular and thick and not stable over a long period of time.

The cationic polymer serves not only as a conditioner, but also enhances the substantivity of the zinc pyrithione. It does this, it is believed, by enhancing the attraction of zinc pyrithione particles for the scalp and hair. The range of cationic polymer used in the present anti-dandruff cream rinse is from about 0.25 to about 5.0% by weight. The amount of cationic polymer most preferred is approximately 1.0% by weight.

Other cationic polymers can be substituted for Quaternium 41, though they are less preferred and do not yield as cosmetically attractive commercial preparation. The following are alternative cationic polymers which we have found effective in place of Quaternium 41 and which are readily compatible in suspension with zinc pyrithione, in the presence of glucan gum or guar gum or mixtures thereof, and hydroxyethylcellulose:

Quaternium 23, which is a quaternary ammonium polymer formed by the reaction of dimethyl sulfate and a copolymer of vinyl pyrrolidone and dimethyl aminoethylmethacrylate;

Quaternium 40, which is a highly charged cationic dimethyldiallyl ammonium chloride homopolymer.

Quarternium 19, which is a polymer of hydroxyethyl cellulose reacted with epichlorohydrin and then quaternized with trimethyl amine; and Polyquaternium 3, which is a copolymer of trimethylammonium ethyl methacrylyte methosulfate and acrylimide.

It is obvious, to one skilled in the art, that alternative polymers may be substituted. Quaternium 42, for example, is a likely candidate for use as the cationic polymer. The names used are, as in the case of Quaternium 41, found in the C.T.F.A. Cosmetic Ingredient Dictionary, Second Edition.

Zinc pyrithione must be employed in the finished product at such a level so as to provide effective, clinically demonstrable, dandruff control. Prior artisans have stated that anywhere from 0.1 to 10% by weight zinc pyrithione should be used. As a practical matter, probably more than 5% would be redundant and in most shampoos, approximately 2% active zinc pyrithione is optimum. Thus, the preferred embodiment employs from about 0.25% to about 5% by weight active zinc pyrithione. Most preferably, about 1% active zinc pyrithione is used. The word "active" refers to the fact that zinc pyrithione usually comes in aqueous dispersion such that the level of "active" zinc pyrithione will be somewhat less than the percentage of the total dispersion added to the formulation. Hence 2.1% by weight of a 48% zinc pyrithione dispersion would actually constitute 1% active zinc pyrithione by weight.

The suspension system for the product of the preferred embodiment comprises a combination of (1) hydroxyethylcellulose and (2) glucan gum, or guar gum or mixtures thereof. This combination is the only one found which works commercially satisfactorily. This is particularly surprising in view of the fact that this combination was not effective in suspending zinc pyrithione and a cationic polymer in a shampoo formulation.

In this regard, it will of course be appreciated that by using excessive amounts of conventionally known suspensing agents, almost any such conventional suspension agent will keep zinc pyrithione in suspension in the presence of a cationic polymer. However, as a practical commercial matter, such products would be far too thick, or would lose effectiveness due to flocculation of the cationic polymer which may be masked by the thickness of the product, or would be too expensive or a combination of these. By using the combination of hydroxyethylcellulose and glucan gum or guar gum or a mixture of both, one can control both the viscosity and aesthetic qualities of the cream rinse conditioner very accurately.

Preferably, the suspension combination comprises from 25 to 75% hydroxyethylcellulose and conversely from 75 to 25% of the gum. Most preferably, the two ingredients are employed in equal proportions by weight. From about 0.5 to about 5% of the suspension combination is utilized in the product, and most preferably about 1%. hence, it is most preferable that 0.5% glucan gum or guar gum or a mixture thereof and 0.5% hydroxyethylcellulose are used in the final product.

Glucan and guar gum are high molecular weight, linear, nonionic polysaccharides. While they can be modified to be made cationic or anionic, or to be made nonlinear, such modifications are not desirable in the context of the present invention.

The glucan gum and guar gum used must be of a refined grade. Thus, it is has been found that a refined grade of glucan gum in powder form with a white to cream clear appearance, and having 90% glucan content and only 3% ash and 0.4% nitrogen works very effectively in the present invention. On the other hand, so-called industrial quality glucan gum which contains only 65% glucan is not operable. This compound is a more cream color powder, has 4% ash and 2.5% nitrogen. In a 1% solution, the industrial quality glucan gum shows a viscosity at 30 rpm Brookfield LVF viscometer, Spindle No. 3, viscosity of 1,000 to 1,200, whereas the refined grade has a viscosity of 2,100 to 2,400.

Similarly, the guar gum used should be a similarly highly purified or refined powder. Its viscosity at 25 degrees C. on the Brookfield viscometer, Model RVF, in a 1% solution should be approximately 4,500 cps.

Up to 18% of other conditioning agents can be employed in the cream rinse formulation. Most preferably, approximately 9% of other conditioners are employed. One such conditioner is a commercially available mixture of stearyl alcohol and cetrimonium bromide. This product comprises about 75% stearyl alcohol and 25% cetrimonium bromide. From 1 to 5% of this ingredient, and preferably around 3% of this ingredient is employed. Up to 4%, and preferably about 2% steartrimonium hydrolyzed animal protein is also utilized. Up to 8% and preferably about 4% isostearamido propyl morpholine lactate is additionally employed as a conditioning agent in the most preferred embodiment.

Other conventional conditioning agents can be substituted into the formula. Thus, we have employed, as alternatives to stearyl alcohol and cetrimonium bromide, stearalkonium chloride, tallow amidoethyl polyhydroxy ether ammonium chloride, hydrogenated tallow polyoxyethylene ammonium ethosulfate, cetrimonium chloride and dialkyl dimethyl ammonium chloride, and other quaternary ammonium salts typically used in cream rinse conditioners. These are all known cream rinse conditioning agents and it is believed that their interchangeability as well as the possibility of using numerous substitutes and the reasons for using one or more are well-known in the art.

Items such as jojoba oil and perfume are optional in the formula. It is preferred that deionized water be used in formulating the composition. Other ingredients will undoubtedly occur to those skilled in the art for possible inclusion in a product made in accordance with the present invention.

The following is believed to be the most preferred formulation for a commercial product:

| MATERIAL | % BY WEIGHT |
| --- | --- |
| Deionized water | 86.0 |
| Hydroxyethylcellulose | 0.5 |
| Glucan gum or guar gum or a mixture thereof | 0.5 |
| Steartrimonium Hydrolyzed Animal Protein | 2.0 |
| Stearyl Alcohol and Cetrimonium Bromide (75/25) | 3.0 |
| Isostearamido Propyl Morpholine Lactate | 4.0 |
| Quaternium 41 (supplied by Merck & Co. in an 8% aqueous solution) | 1.0 |
| Jojoba Oil | 0.5 |
| Zinc Pyrithione (48% dispersion) | 2.1 (1% active) |
| Perfume | 0.4 |
| Total | 100.0% |

The resulting formulation is smooth, consistent and stable. Accelerated aging tests have determined the product to be very stable, providing a uniform drug (active) dosage to the consumer even with aging. One does not even have to include an instruction to shake this composition before using to insure homogenity. It appears to be very stable (homogeneous) for long periods of time, requiring no expiration date on the container.

The conclusions reached in connection with the present invention are supported by extensive experimental data. The following tables summarize that data (with some of the experiments reported actually being based on more than one attempt). In all cases, the quantities of zinc pyrithione used were 1 to 2% active. The quantities of all other ingredients expressed in these tables were from 0.5 to 2%, usually 1%.

TABLE I

FORMULATIONS IN ACCORDANCE WITH THE PRESENT INVENTION

| MIXTURE | RESULT |
| --- | --- |
| Quaternium 41, hydroxyethylcellulose, glucan gum and zinc pyrithione | very stable composition, very smooth, with less suspension agent required than to achieve any kind of stability with any other suspending agents. Better long term stability than with other suspending agents. |
| Quaternium 40, hydroxyethylcellulose, glucan gum and zinc pyrithione | Same as above, except that the product did not have as nice an aesthetic, cosmetic appearance as when Quaternium 41 was employed above. |
| Quaternium 23, hydroxyethylcellulose, glucan gum and zinc pyrithione | About the same as above when Quaternium 40 was used. |
| Polyquaternium 3, hydroxyethylcellulose, glucan gum and zinc pyrithione | About the same as above when Quaternium 40 was used. |
| Polyquaternium 19, hydroxyethylcellulose, glucan gum and zinc pyrithione | About the same as above when Quaternium 40 was used. |
| Quaternium 41, hydroxyethylcellulose, guar gum and zinc pyrithione | very smooth, clean, and has good stability. Very comparable to the first example above. |

The last test actually reflects work with three different commercially available guar gums. All operated comparably in conjunction with hydroxyethylcellulose to give the results reported.

TABLE II

FORMULATIONS USING QUATERNIUM 41 ZINC PYRITHIONE AND OTHER SUSPENSION AGENTS

| MIXTURE | RESULTS |
| --- | --- |
| Cellulose thickener (trademark product Avicel GLG11), Quaternium 41 and zinc pyrithione | Inconsistent, sometimes granular, sometimes just barely acceptable, at least initially, though product tended to separate on long term aging. |
| Cellulose (Avicel as above), an acrylic polymer thickener, (known commercially as Permazorb), Quaternium 41 and zinc pyrithione | Lumpy. |
| Hydroxypropylmethylcellulose (known commercially as Methocel), Quaternium 41 and zinc pyrithione | Stable, but difficult to formulate. Requires heating the water to 176 degrees F., then dispersing the Methocel, then cooling the water until it dissolves and then adding other ingredients. Also, the product tended to separate with long term aging. |
| Quaternium 19 as the suspension agent, Quaternium 41 and zinc pyrithione | The mixture was not compatible, with |

TABLE II-continued
FORMULATIONS USING QUATERNIUM 41 ZINC PYRITHIONE AND OTHER SUSPENSION AGENTS

| MIXTURE | RESULTS |
|---|---|
| Xanthan gum, hydroxyethylcellulose, Quaternium 41 and zinc pyrithione | severe flocculation resulting. Noticeable incompatibility of the ingredients and poor stability. |
| Hydroxypropylmethylcellulose, hydroxyethylmethylcellulose, Quaternium 41 and zinc pyrithione | The material was hard to work with and had poor stability. |
| Hydroxyethylcellulose alone as the suspension agent, Quaternium 41 and zinc pyrithione | Smooth material, but poor stability. |
| Locust bean gum, hydroxyethylcellulose, Quaternium 41 and zinc pyrithione | Some difficulty in hydrating the product, and the product had marginal stability. Tends to lump. |
| Guar gum used alone as the suspension agent, Quaternium 41 and zinc pyrithione | Does operate to bring the composition into suspension, but is not satisfactorily aesthetically pleasing. |
| Glucan gum used as the suspending agent alone, Quaternium 41 and zinc pyrithione | Does operate to bring the composition into suspension, but is not satisfactorily aesthetically pleasing. |
| Guar gum and hydroxypropylmethylcellulose, Quaternium 41 and zinc pyrithione | Not acceptable, separates on aging. |
| Sodim carboxymethylcellulose, Quaternium 41 and zinc pyrithione | Ingredients not compatible |

In tests related to those set forth in Table II, Avicel and Quaternium 41 were tested without zinc pyrithione, and Methocel and Avicel were tested with zinc pyrithione but without Quarternium 41. The Avicel and Quaternium 41 were found incompatible. The Methocel and Avicel and zinc pyrithione without Quarternium 41 gave inconsistent results, with the product tending to be unstable, or at least tending to separate on long term aging.

TABLE III
OTHER CATIONIC POLYMERS AND OTHER SUSPENSION AGENTS

| MIXTURE | RESULTS |
|---|---|
| Magnesium aluminum silicate thickener (sold as Veegum), Quaternium 19 and zinc pyrithione | Flocculation. |
| Magnesium aluminum silicate thickener (sold as Veegum) hydroxypropyl cellulose thickener (sold as Klucel), Quaternium 19 and zinc pyrithione | Flocculation. |
| Cellulose thickener (Avicel CLG11), a cationic cellulosic polymer (sold as Polymer LR), and zinc pyrithione | Incompatible. |
| A cationic acrylic polymer (sold as Reten Spx), cellulose thickener (Avicel GLG11), and zinc pyrithione | Flocculation. |
| Magnesium aluminum silicate (Veegum), Quaternium 40 and zinc pyrithione | Separation in four days at ambient conditions. |
| Magnesium aluminum silicate (Veegum), Quaternium 40, zinc pyrithione and hydroxypropyl cellulose (Klucel) | Lumpy. |
| Magnesium aluminum silicate (Veegum), hydroxypropyl methylcellulose (Methocel), Polyquaternium ammonium chloride, a cationic polymer sold as Mirapol A-15) and zinc pyrithione | Flocculation. |
| Cellulose thickener (Avicel GLG11), polyquaternium ammonium chloride, a cationic polymer (sold as Mirapol A-15) and zinc pyrithione | Not compatible. |
| Polyquaternium-3, (a cationic polymer sold as Catamer Q), cellulose thickener (Avicel GL11), zinc pyrithione | Granular and inconsistent, with long term aging being a problem and tending to result in separation. |
| Polyquaternium ammonium chloride, (a cationic polymer sold as Mirapol A-15; an acrylic polymer thickener sold as Permazorb), and zinc pyrithione | Not compatible. |
| Magnesium silicate thickener (sold as Laponite XLS) and Quaternium 22 (a cationic polymer sold as Ceraphyl 60) | These were incompatible even before the zinc pyrithione was added |
| Magnesium aluminum silicate thickener, hydroxypropyl methylcellulose thickener, Quaternium 22 cationic polymer and zinc pyrithione | Flocculation. |
| Magnesium aluminum silicate thickener, hydroxypropyl methylcellulose thickener and polyquaternium ammonium chloride (Mirapol A-15) | Separation occurred even before the zinc pyrithione was added. |
| Propylene glycol alginate thickener (sold as Kelecoid HVF), polyquaternium-3 and zinc pyrithione | Separates. |
| Cellulose thickener (Avicel GLG11), Quaternium 22, Quaternium 26 (sold as Cerophyl 65) and zinc pyrithione | Separates. |
| Hydroxypropyl methylcellulose thickener, polyquaternium-3 cationic polymer, Quaternium 22 cationic polymer and zinc pyrithione | Separation. |
| Hydroxypropyl methylcellulose thickener, polyquaternium-3 and zinc pyrithione | Separates. |

Other tests were conducted in conjunction with this invention, but tended to focus on combinations of suspending agents and zinc pyrithiones alone, without cationic polymers or alternatively on combinations of suspending agents with cationic polymers. None of the results of these further tests are considered sufficiently pertinent to report herein.

It is believed that the criticality of the suspension system in accordance with the present invention, for effecting a cream rinse conditioner including zinc pyrithione and a cationic polymer is illustrated by the above test results. In a narrower aspect of the invention, the superiority of Quaternium 41 in a zinc pyrithione anti-dandruff rinse conditioner is also surprisingly illustrated, even though Quaternium 41 cannot be satisfactorily formulated in an anti-dandruff shampoo formulation using zinc pyrithione. Of course it is understood that alternative cationic polymers can be utilized in a commercially acceptable product in accordance with broader aspects of the invention.

It will also be appreciated that various substitutions and modifications can be made without departing from the spirit and broader aspects of the invention, as set forth more particularly in the appended claims. Also it will be appreciated that while the term "rinse conditioner" is used herein in describing this invention, it is understood that rinse conditioners are called by many names in the marketplace. Our invention may be classified as a rinse conditioner, a conditioning rinse, a cream rinse, a rinse, a conditioner, a cream rinse conditioner, a cream rinse, and a cream rinse conditioner, for example.

The embodiments of the invention in which an exclusive property or privilege is claimed are defined as follows:

1. In an improved zinc pyrithione water base anti-dandruff cream rinse conditioner having improved zinc pyrithione suspension wherein the improvement comprises:

the combination of from about 0.25 to about 5% by weight zinc pyrithione to provide an effective anti-dandruff agent, from about 0.25% to about 5% of by weight a cationic polymer and from about 0.5 to about 4% by weight of a combination of (1) one of glucan gum, guar gum or mixtures thereof wherein the glucan gum is a refined gum in powder form with a white to cream clear appearance, and having 90% glucan content, only 3% ash, 0.4% nitrogen and a viscosity of 2,100 to 2,400 and the guar gum is refined and having a viseosity at 25 degrees C. on the Brookfield viscometer, model RVF, in a 1% solution should be approximately 4,500 cps and (2) hydroxyethylcellulose, wherein said combination ingredients (1) and (2) have a proportional relationship of from about 3:1 to about 1:3 by weight with respect to one another.

2. The anti-dandruff rinse conditioner of claim 1, wherein said combination ingredients (1) and (2) are present in approximately equal proportions by weight with respect to one another.

3. The anti-dandruff rinse conditioner of claim 1 wherein said percentages by weight comprise preferably:
about 1% by weight active zine pyrithione;
about 1% by weight of said cationic polymer; and
about 1% by weight of said combination of ingredients (1) and (2).

4. The anti-dandruff rinse conditioner of claim 1 in which said cationic polymer is an acrylamide copolymer of dimethyldiallyl ammonium chloride.

5. The anti-dandruff rinse of claim 4 in which said cationic acrylamide copolymer of dimethyldiallyl ammonium chloride has a molecular wieght of approximately 500,000.

6. The anti-dandruff rinse conditioner of claim 1 which includes additional conditioning ingredients.

7. The anti-dandruff rinse conditioner of claim 6 wherein said additional conditioning agents are selected from the group consisting of a mixture of stearyl alcohol and cetrimonium bromide, steartrimonium hydrolyzed animal protein, isostearamido propyl morpholine lactate, stearalkonium chloride, tallow amidoethyl polyhydroxy ether ammonium chloride, hydrogenated tallow poly oxyethylene ammonium ethosulfate, cetrimonium chloride, dialkyl dimethyl ammonium chloride, and other quaternary ammonium salts, and combinations thereof.

8. The anti-dandruff cream rinse conditioner of claim 7 wherein said additional conditioning agents are present in an amount of up to about 18%.

9. The anti-dandruff rinse conditioner of claim 8 wherein said amount by weight of said additional conditioning agents is approximately 9%.

10. The anti-dandruff rinse conditioner of claim 7 in which said cationic polymer is an acrylamide copolymer of dimethyldiallyl ammonium chloride.

11. The anti-dandruff rinse of claim 10 in which said cationic acrylamide copolymer of dimethyldiallyl ammonium chloride has a molecular weight of approximately 500,000.

12. The anti-dandruff rinse conditioner of claim 1 wherein said percentages by weight comprise:
from about 0.25 to about 5.0% by weight active zinc pyrithione;
from about 0.25 to about 5% by weight of a cationic polymer selected from the group consisting of Quaternium 41, Quaternium 19, Quaternium 23, Quaternium 40 and Polyquaternium 3, and/or combination thereof; and
from about 0.5 to about 4% by weight of the combination of (1) one of glucan gum, guar gum or mixtures thereof, and (2) hydroxyethylcellulose in proportions by weight to one another of from about 3:1 to about 1:3.

13. The anti-dandruff rinse conditioner of claim 12 which additionally includes up to about 18% of additional conditioning agents.

14. The anti-dandruff rinse conditioner of claim 13 wherein said additional conditioning agents are selected from the group consisting of: a mixture of stearyl alcohol and cetrimonium bromide, steartrimonium hydrolyzed animal protein, isostearamido propyl morpholine lactate, stearalkonium chloride, tallow amidoethyl polyhydroxy ether ammonium chloride, hydrogenated tallow polyoxyethylene ammonium ethosulfate, cetrimonium chloride, dialkyl dimethyl ammonium chloride and other quaternary ammonium salts, and combinations thereof.

15. The anti-dandruff rinse conditioner of claim 14 wherein said additional conditioning agents include at least said combination of stearyl alcohol and cetrimonium bromide in an amount of from about 1 to about 5% by weight.

16. The anti-dandruff rinse conditioner of claim 15 wherein said combination of stearyl alcohol and cetrimonium bromide is present in an amount of about 3% by weight.

17. The anti-dandruff rinse conditioner of claim 12, 13, 14, 15 or 16 in which said cationic polymer is an acrylamide copolymer of dimethyldiallyl ammonium chloride.

18. The anti-dandruff rinse of claim 17 in which said cationic acrylamide copolymer of dimethyldiallyl ammonium chloride has a molecular weight of approximately 500,000.

19. The anti-dandruff rinse conditioner of claim 12, 13, 14, 15 or 16 wherein said composition comprises:
about 1% by weight of active zinc pyrithione;
about 1% by weight of said cationic polymer;
about 0.5% by weight of one of said glucan gum, guar gum or mixtures thereof; and
about 0.5% by weight of said hydroxyethylcellulose.

20. The anti-dandruff rinse conditioner of claim 19 in which said cationic polymer is an acrylamide copolymer of dimethyldiallyl ammonium chloride.

21. The anti-dandruff rinse of claim 20 in which said cationic acrylamide copolymer of dimethyldiallyl ammonium chloride has a molecular weight of approximately 500,000.

22. The anti-dandruff rinse conditioner of claim 12, 13, 14, 15 or 16 in which said combination ingredients (1) and (2) are present in a ratio of about 1:1 by weight.

23. The anti-dandruff rinse conditioner of claim 22 in which said cationic polymer is an acrylamide copolymer of dimethyldiallyl ammonium chloride.

24. The anti-dandruff rinse of claim 23 in which said cationic acrylamide copolymer of dimethyldiallyl ammonium chloride has a molecular weight of approximately 500,000.

25. The anti-dandruff conditioner rinse of claim 24 wherein said composition comprises:
   about 1% by weight of active zinc pyrithione;
   about 1% by weight of said cationic polymer;
   about 0.5% by weight of said glucan gum, guar gum or mixtures thereof; and
   about 5% by weight of said hydroxyethylcellulose.

26. The anti-dandruff rinse conditioner of claim 23 wherein said composition comprises:
   about 1% by weight of active zinc pyrithione;
   about 1% by weight of said cationic polymer;
   about 0.5% by weight of said glucan gum, guar gum or mixtures thereof; and
   about 0.5% by weight of said hydroxyethylcellulose.

27. The anti-dandruff rinse conditioner of claim 22 wherein said composition comprises:
   about 1% by weight of active zinc pyrithione;
   about 1% by weight of said cationic polymer;
   about 0.5% by weight of said glucan gum, guar gum or mixtures thereof; and
   about 5% by weight of said hydroxyethylcellulose.

* * * * *

UNITED STATES PATENT AND TRADEMARK OFFICE
CERTIFICATE OF CORRECTION

PATENT NO. : 4,557,928

DATED : December 10, 1985

INVENTOR(S) : David Alan Glover

It is certified that error appears in the above-identified patent and that said Letters Patent is hereby corrected as shown below:

Column 2, line 50:

"acive" should be --active--

Column 4, lines 24 & 25:

"suspensing" should be --suspending--

Column 4, line 43:

"hence" should be --Hence--

Column 8, line 17:

"GL11" should be --GLG11--

Column 8, line 22:

after "A-15" insert --)--

Column 8, line 23:

before "sold" insert --(--

Column 8, line 39:

"Cellulosc" should be --Cellulose--

UNITED STATES PATENT AND TRADEMARK OFFICE
CERTIFICATE OF CORRECTION

PATENT NO. : 4,557,928

DATED : December 10, 1985

INVENTOR(S) : David Alan Glover

It is certified that error appears in the above-identified patent and that said Letters Patent is hereby corrected as shown below:

Column 9, line 43:

"zine" should be --zinc--

Signed and Sealed this

Sixth Day of May 1986

[SEAL]

Attest:

DONALD J. QUIGG

Attesting Officer

Commissioner of Patents and Trademarks